United States Patent [19]

Gray

[11] Patent Number: 5,627,183

[45] Date of Patent: May 6, 1997

[54] METHODS FOR TREATING URTICARIA USING OPTICALLY PURE (+) CETIRIZINE

[75] Inventor: Nancy M. Gray, Marlboro, Mass.

[73] Assignee: Sepracor, Inc., Marlborough, Mass.

[21] Appl. No.: 622,617

[22] Filed: Mar. 26, 1996

Related U.S. Application Data

[63] Continuation of Ser. No. 167,722, Dec. 15, 1993, abandoned, which is a continuation of Ser. No. 950,910, Sep. 24, 1992, abandoned.

[51] Int. Cl.$^6$ ............................................. A61K 31/495
[52] U.S. Cl. ........................................................ 514/255
[58] Field of Search ........................................... 514/255

[56] References Cited

U.S. PATENT DOCUMENTS

| | | | |
|---|---|---|---|
| 4,525,358 | 6/1985 | Baltes et al. | 514/255 |
| 4,829,064 | 5/1989 | Sunshine et al. | 514/255 |
| 5,478,941 | 12/1995 | Cossement et al. | 544/383 |

FOREIGN PATENT DOCUMENTS

| | | |
|---|---|---|
| 2225320 | 5/1990 | United Kingdom . |
| 2225321 | 5/1990 | United Kingdom . |

OTHER PUBLICATIONS

De Vos & Maleux et al., Ann. Allergy, 59(4), 278–82, 1987.
De Vos & Joseph et al., Int. Arch. Allergy Appl. Immunol., 88(1–2), 212–15, 1989.
Gong et al., 90:243620 Biosis, BA89:130573, 1990.
Cossement et al., CA 113(21): 191396t Chemical Abstracts, 1990.
Schoeffter et al. "Competative and stereoselective histamine $H_1$ antagonistic effect..." *Eur. J. Parmacol.*, 136, 235–237 (1987).
Fricke et al. "Fortschritte für die Arzneimitteltherapie?" *Neue Arzneimittel 1990/1991*, 14–21 (1991).
E.J. Ariëns "Racemische Therapeutica Probleemiddelen" *Pharmaceutisch Weekblad*, 125 552–554 (1990).
E.J. Ariëns "Stereoselectivity in pharmacodynamics and pharmacokinetics" *Schweiz. Med. Wochenschr.*, 120 131–134 (1990).
B. Testa et al. "Racemates Versus Enantiomers in Drug Development: Dogmatism or Pragmatism?" *Chirality*, 2 129–133 (1990).
E.J. Ariëns "Racemic therapeutics—ethical and regulatory aspects" *Eur. J. Clin. Pharmacol.*, 41 89–93 (1991).

*Primary Examiner*—William R. A. Jarvis
*Attorney, Agent, or Firm*—Heslin & Rothenberg, P.C.

[57] ABSTRACT

Methods are disclosed utilizing optically pure (+) cetirizine for the treatment of urticaria in humans while avoiding the concomitant liability of adverse effects associated with the racemic mixture of cetirizine.

6 Claims, No Drawings

METHODS FOR TREATING URTICARIA USING OPTICALLY PURE (+) CETIRIZINE

CROSS REFERENCE TO RELATED APPLICATIONS

This application is a continuation of application Ser. No. 08/167,722 filed Dec. 15, 1993, now abandoned, which is a continuation of application Ser. No. 07/950,910, filed Sep. 24, 1992, now abandoned.

BACKGROUND OF THE INVENTION

This invention relates to novel compositions of matter containing optically pure (+) cetirizine. These compositions possess potent activity in treating seasonal and perennial allergic rhinitis, the symptoms of allergic asthma, chronic idiopathic urticaria, some types of physical urticaria, and other disorders including those that would benefit from an inhibitory action on eosinophil function. (+) Cetirizine inhibits eosinophil chemotaxis and function and the generation of cytotoxic mediators by blood platelets, providing therapy in immunologically-induced asthma with particular utility in the late phase of the disease episode. Optically pure (+) cetirizine provides this treatment while avoiding adverse effects, including, but not limited to, sedation and somnolence, headache, gastrointestinal disturbance, anticholinergic effects, dizziness, cardiac arrhythmias and other cardiovascular effects which are associated with the administration of the racemic mixture of cetirizine. Also disclosed are methods for treating the above described conditions in a human while avoiding the adverse effects that are associated with the racemic mixture of cetirizine by administering the (+) isomer of cetirizine to said human.

The active compound of these compositions and methods is an optical isomer of cetirizine, the preparation of which is described in U.S. Pat. No. 4,525,358 (Baltes et al.). The medicinal chemistry of cetirizine is described by Campoli-Richards et al., [Drugs 40, 762–781 (1990)], Snyder and Snowman [*Allergy* 59 II, 4–8 (1987)], and Rihoux and Dupont [pu Annals of Allergy 59, 235–238 (1987)]. Chemically, the active compound is the (+) isomer of 2-[4-[(4-chlorophenyl)phenylmethyl]-1-piperazinyl] ethoxyacetic acid, hereinafter referred to as cetirizine.

(+) Cetirizine, which is the subject of the present invention, is not presently commercially available; only the 1:1 racemic mixture is commercially available as its dihydrochloride salt.

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. There is no correlation between nomenclature for the absolute stereochemistry and for the rotation of an enantiomer. Thus, D-lactic acid is the same as (−) lactic acid, and L-lactic acid is (+). For a given chemical structure, these chiral compounds exist as a pair of enantiomers which are identical except that they are non-superimposable mirror images of one another. A specific stereoisomer may also be referred to as an enantiomer, and a mixture of such isomers is often called an enantiomeric or racemic mixture.

Stereochemical purity is of importance in the field of pharmaceuticals, where 12 of the 20 most prescribed drugs exhibit chirality. A case in point is provided by the L-form of the beta-adrenergic blocking agent, propranolol, which is known to be 100 times more potent than the D-enantiomer.

Furthermore, optical purity is important since certain isomers may actually be deleterious rather than simply inert. For example, it has been suggested that the D-enantiomer of thalidomide was a safe and effective sedative when prescribed for the control of morning sickness during pregnancy, while the corresponding L-enantiomer has been believed to be a potent teratogen. The synthesis of (+) cetirizine and (−) cetirizine are described in British application 2,225,321, but no pharmacology of individual enantiomers is reported.

The racemic mixture of cetirizine is presently used primarily in seasonal and perennial allergic rhinitis. The symptomatology of immediate-type allergic diseases, including allergic rhinitis, presumably results from the antigen-induced release of various pharmacologically active substances from mast cells, and from basophilic leukocytes. The substances thus released from these cells, and possibly others as well, are referred to as primary mediators of anaphylaxis and include, among others, histamine. The acute seasonal form of allergic rhinitis, hay fever, and perennial allergic rhinitis are characterized by sneezing, rhinorrhea, nasal congestion, pruritus, conjunctivitis and pharyngitis. In acute seasonal rhinitis, the nose, roof of the mouth, eyes and pharynx often itch, and lacrimation, sneezing and clear, watery nasal discharge follow the pruritus. Additionally, frontal headaches, irritability, anorexia, depression and insomnia may occur. In perennial rhinitis, chronic nasal obstruction is often prominent and may extend to eustachian tube obstruction. For most patients, topical corticosteriods, some aerosol vasoconstrictor agents, and long acting antihistamine agents provide significant relief of symptoms. The action of cetirizine on non-immunologically (non IgE) mediated hypersensitivity reactions has been less clear although there are some suggestions of activity in the treatment of exercise induced asthma, cold urticaria, and non-specific bronchial hyperreactivity.

Racemic cetirizine dihydrocholoride is an orally active, potent, long acting peripheral histamine $H_1$ receptor antagonist. The compound is one of the second generation of $H_1$ histamine receptor antagonists which generally offer some significant advantages beyond the first generation compounds. The advantages include (1) less sedation, (2) little anticholinergic activity and (3) longer duration, which improves patient compliance. In addition to being competitive inhibitors of histamine at the end organ site, second generation $H_1$ histamine inhibitors appear to have other anti-allergic pharmacologic mechanisms which have led to their use in bronchial asthma, as well as in seasonal and perennial rhinitis and the chronic urticarias.

Experiments ex vivo suggest that racemic cetirizine does not significantly penetrate the blood brain barrier. It has been suggested therefore that cetirizine's ability to provide a reduced incidence of sedative side effects may result in part from its receptor selectivity and in part from its relative exclusion from the CNS. Other experiments have suggested that cetirizine does not inhibit mast cell activation but rather that it antagonizes the action of histamine once released from the mast cell following antigen or chemical stimulation. There are also reports that racemic cetirizine inhibits the degranulation of human basophils induced by anti IgE. Cetirizine has been shown to inhibit the chemotaxis of eosinophils to the tissues where they would otherwise contribute to the pathogenesis of asthma.

Cetirizine is rapidly absorbed upon oral administration and although food may slightly reduce the rate of absorption, the extent is not affected. The compound is bound to plasma proteins and peak cetirizine concentrations in the brain are less than 10% that of the plasma concentration. Cetirizine is excreted in the urine largely as unchanged drug and the elimination half-life is roughly 7 to 10 hours.

The racemic mixture of cetirizine may be useful in treating other disorders such as allergic pulmonary disease and particularly in treating the symptoms of allergic bronchial asthma. Patients who suffer from allergic bronchial asthma develop such clinical symptoms as wheezing and dyspnea after exposure to allergens, environmental irritants, viral infections, cold air and exercise. Many of the symptoms result from smooth muscle contraction and vascular dilatation, which, in turn, result from mediator release when the antigen reacts with the IgE antibody on the surface of a mast cell or basophil. This serves as a basis for the use of histamine $H_1$ antagonists.

In addition, racemic cetirizine may be useful for treating chronic idiopathic urticaria and some types of physical urticaria. Urticaria is characterized by local wheals and erythema in the dermis; acute urticaria is essentially an anaphylaxis that is limited to the skin and subcutaneous tissues. The condition may arise from food allergy, drug allergy, insect sting, or the like, and is distinct from chronic or idiopathic urticaria which may last for several weeks and can only rarely be associated with a specific cause. Because these urticarias appear in many cases to be IgE antibody mediated, many of the symptoms may be treated with a histamine $H_1$ receptor antagonist such as cetirizine. The direct inhibition of eosinophil chemotaxis by cetirizine may also provide therapy to the late phase of allergic episodes in disorders such as allergic asthma, allergic rhinitis, and in other conditions characterized by eosinophilia.

Many of the second generation histamine $H_1$ receptor antagonists offer advantages over the first generation of histamine antagonists in that there is reduced sedation and anticholinergic activity. Nonetheless, some adverse effects remain, including, but not limited to, some incidence of sedation and somnolence; cardiovascular effects including arrhythmias; headache; gastrointestinal disturbances; dizziness and nausea. The racemic mixture of cetirizine has been found to cause many of these adverse effects, including sedation and somnolence. Thus, it would be particularly desirable to find a compound with the advantages of the racemic mixture of cetirizine which would not have the aforementioned disadvantages.

SUMMARY OF THE INVENTION

It has now been discovered that the optically pure (+) isomer of cetirizine is an effective agent for treating seasonal and perennial allergic rhinitis, the symptoms of allergic asthma, chronic idiopathic urticaria, some physical urticaria, and other disorders, including those that would benefit from an inhibitory action on eosinophilia, and eosinophil function. The optically pure (+) isomer of cetirizine provides this effective treatment while avoiding the adverse effects including, but not limited to, sedation and somnolence, headache, gastrointestinal disturbance, dizziness, nausea, cardiac arrhythmias and other cardiovascular effects. The present invention also includes methods for treating the above described conditions in a human while avoiding the adverse effects that are associated with the racemic mixture of cetirizine by administering the optically pure (+) isomer of cetirizine to said human.

DETAILED DESCRIPTION OF THE INVENTION

The present invention encompasses a method of treating the symptoms of seasonal and perennial allergic rhinitis in a human, which comprises administering to a human in need of such symptomatic relief therapy, an amount of (+) cetirizine, or a pharmaceutically acceptable salt thereof, substantially free of its (−) stereoisomer, said amount being sufficient to alleviate the symptoms of seasonal and perennial allergic rhinitis. The method avoids the concomitant liability of adverse effects associated with the administration of the racemic compound by providing an amount which is insufficient to cause the adverse effects associated with the racemic mixture of cetirizine.

The present invention also encompasses an antirhinitis composition for the treatment of a human in need of antirhinitis therapy, which comprises an amount of (+) cetirizine, or a pharmaceutically acceptable salt thereof, substantially free of its (−) stereoisomer, said amount being sufficient to alleviate said rhinitis but insufficient to cause the adverse effects associated with racemic cetirizine.

The present invention further encompasses a method of treating allergic asthma and chronic and physical urticaria in a human, which comprises administering to a human in need of such asthma or urticaria therapy, an amount of (+) cetirizine, or a pharmaceutically acceptable salt thereof, substantially free of its (−) stereoisomer, sufficient to alleviate said asthma or urticaria. The method avoids the concomitant liability of adverse effects associated with the administration of racemic cetirizine by providing an amount which is insufficient to cause adverse effects associated with the administration of racemic cetirizine.

In addition, the present invention encompasses an antiallergic and antiurticaric composition for the treatment of a human having allergic asthma, chronic idiopathic urticaria and some types of physical urticaria, which comprises an amount of (+) cetirizine, or a pharmaceutically acceptable salt thereof, substantially free of its (−) isomer, said amount being sufficient to alleviate or palliate said disorder but insufficient to cause adverse effects associated with the administration of racemic cetirizine.

A further aspect of the present invention includes a method of treating a condition caused by or contributed to by an eosinophilia or enhanced eosinophil function in a human, which comprises administering to a human in need of such therapy, an amount of (+) cetirizine, or a pharmaceutically acceptable salt thereof, substantially free of its (−) stereoisomer, sufficient to alleviate said eosinophilia or enhanced eosinophilia function. The method avoids the concomitant liability of adverse effects associated with the administration of racemic cetirizine by providing an amount which is insufficient to cause adverse effects associated with the administration of racemic cetirizine. Conditions associated with an eosinophilia or an altered eosinophil function in humans may include, but are not limited to, allergic asthma, seasonal allergic rhinitis, atopic dermatitis, some parasitic diseases, and chronic obstructive lung disease with no demonstrable evidence of allergic asthma. Moreover accumulations of eosinophils in both the gastrointestinal and genitourinary tracts indicate the desirability of regulation of eosinophil function in disorders of these tracts.

Furthermore, the present invention includes a composition for treating disorders associated with or enhanced by an eosinophilia or enhanced eosinophil function that would benefit from a potent inhibitor of eosinophil chemotaxis in a human which comprises an amount of (+) cetirizine, or a pharmaceutically acceptable salt thereof, substantially free of its (−) stereoisomer, said amount being sufficient to alleviate said condition associated with an eosinophilia or altered eosinophil function, but insufficient to cause adverse effects associated with the administration of racemic cetirizine.

The available racemic mixture of cetirizine (i.e. a 1:1 racemic mixture of the two enantiomers) exhibits antihistaminic activity through its selective and potent binding to histamine $H_1$ peripheral receptor sites and causes inhibition of eosinophil chemotaxis thus providing therapy and a reduction of symptoms in a variety of conditions and disorders related to allergic rhinitis, allergic asthma, several types of urticaria, and conditions related to eosinophilia; however, this racemic mixture, while offering the expectation of efficacy, causes adverse effects. Utilizing the optically pure or substantially optically pure isomer of (+) cetirizine results in enhanced efficacy, diminished adverse effects, and accordingly, an improved therapeutic index. It is therefore, more desirable to use the (+) isomer of cetirizine than to administer the racemic mixture.

The term "adverse effects" includes, but is not limited to, sedation and somnolence, headache, gastrointestinal disturbance, dizziness, nausea, cardiac arrhythmias and other cardiovascular effects.

The term "substantially free of its (−) stereoisomer" as used herein means that the compositions contain a greater proportion of the (+) isomer of cetirizine in relation to the (−) isomer of cetirizine. In a preferred embodiment, the term "substantially free of its (−) isomer" as used herein means that the composition comprises at least 90% by weight of (+) cetirizine and 10% by weight or less of (−) cetirizine. In a more preferred embodiment the term "substantially free of the (−) isomer" means that the composition contains at least 99% by weight of (+) cetirizine, and 1% or less of (−) cetirizine. In the most preferred embodiment, the term "substantially free of its (−) stereoisomer" as used herein means that the composition contains greater than 99% by weight of (+) cetirizine. These percentages are based upon the total amount of cetirizine in the composition. The terms "substantially optically pure (+) isomer of cetirizine " or "substantially optically pure (+) cetirizine" and "optically pure (+) isomer of cetirizine" and "optically pure (+) cetirizine" are also encompassed by the above-described amounts.

The term "treating the symptoms of seasonal and perennial rhinitis" as used herein means treating, alleviating or palliating such conditions, and thus providing relief from the symptoms of sneezing, rhinorrhea, nasal congestion, pruritus, conjunctivitis, pharyngitis, lacrimation, frontal headaches, irritability, anorexia, depression, insomnia, eustachian tube obstruction, and the like.

The term "a method for treating allergic asthma and chronic and physical urticaria in a human" as used herein means treating, alleviating or palliating such conditions, and thus providing relief from the symptoms of wheezing, dyspnea, coughing, shortness of breath, respiratory mucus hypersecretion, airway inflammation, local cutaneous wheals, erythema, and the like.

The term, "treating a condition caused by, or contributed to, by an eosinophilia, or enhanced eosinophil function in a human" as used herein means treating, alleviating or palliating such disorders associated with an eosinophilia, thus providing relief from the symptoms of the aforementioned conditions. Allergic asthma, seasonal allergic rhinitis, atopic dermatitis, chronic obstructive lung disease, and symptoms associated with some parasitic diseases, gastrointestinal and genitourinary disorders are among the conditions caused by or contributed to by eosinophilia.

The chemical synthesis of the racemic mixture of cetirizine can be performed by the method described in U.S. Pat. No. 4,525,358 cited above or by an improved procedure disclosed in British application 2,225,320. The (+) isomer of cetirizine may be obtained from its racemic mixture by resolution of the enantiomers of cetirizine or precursors thereto using conventional means such as an optically active resolving acid. For example, British application 2,225,321 (Cossement et al.), which is incorporated herein by reference, discloses a method for resolving the 1-[(4-chlorophenyl)phenylmethyl]piperazine precursor using tartaric acid in ethanol. Other standard methods of resolution known to those skilled in the art including, but not limited to, simple crystallization and chromatographic resolution, can be used. (See for example, E. L. Eliel, *Stereochemistry of Carbon Compounds*, McGraw Hill (1962) and [Wilen and Lochmuller "Tables of Resolving Agents" *Journal of Chromatography* 113, 283–302 (1975)]. Additionally, the optically pure (+) isomer can be prepared from the racemic mixture by enzymatic biocatalytic resolution. See for example U.S. Pat. Nos. 5,057,427 and 5,077,217, the disclosures of which are incorporated herein by reference.

The magnitude of a prophylactic or therapeutic dose of (+) cetirizine in the acute or chronic management of disease will vary with the severity of the condition to be treated and the route of administration. The dose and perhaps the dose frequency will also vary according to the age, body weight and response of the individual patient. In general, the total daily dose range for (+) cetirizine for the conditions described herein is from about 1.0 mg to about 25 mg in single or divided doses. Preferably a daily dose range should be about 2.0 mg to about 20 mg in single or divided doses while most preferably a daily dose range should be about 5 mg to about 10 mg in single or divided doses. In managing the patient, the therapy should be initiated at a lower dose, perhaps at about 2 mg to about 5 mg and increased up to about 10 mg or higher depending on the patient's global response. It is further recommended that children and patients over 65 years and those with impaired renal or hepatic function, initially receive low doses, and that they be titrated based on individual response(s) and blood level(s). It may be necessary to use dosages outside these ranges in some cases as will be apparent to those skilled in the art. Further, it is noted that the clinician or treating physician will know how and when to interrupt, adjust, or terminate therapy in conjunction with individual patient response. The terms "an amount sufficient to alleviate or palliate symptoms of seasonal and perennial allergic rhinitis but insufficient to cause said adverse effects," "an amount sufficient to alleviate or palliate the symptoms of allergic asthma and chronic and physical urticaria but insufficient to cause said adverse effects" and "an amount sufficient to alleviate or palliate the symptoms arising from the eosinophilia of allergic asthma, seasonal allergic rhinitis, atopic dermatitis, parasitic diseases, chronic obstructive lung disease, gastrointestinal and genitourinary disorders but insufficient to cause said adverse effects" are encompassed by the above-described dosage amounts and dose frequency schedule.

Any suitable route of administration may be employed for providing the patient with an effective dosage of (+) cetirizine. For example, oral, rectal, parenteral (subcutaneous, intramuscular, intravenous), transdermal, and like forms of administration may be employed. Dosage forms include tablets, troches, dispersions, suspensions, solutions, capsules, patches, and the like.

The pharmaceutical compositions of the present invention comprise (+) cetirizine as the active ingredient, or a pharmaceutically acceptable salt thereof, and may also contain a pharmaceutically acceptable carrier, and optionally, other therapeutic ingredients.

The terms "pharmaceutically acceptable salts" or "a pharmaceutically acceptable salt thereof" refer to salts prepared from pharmaceutically acceptable non-toxic acids or bases including inorganic acids and bases and organic acids and bases. Since the compound of the present invention is basic, salts may be prepared from pharmaceutically acceptable non-toxic acids including inorganic and organic acids. Suitable pharmaceutically acceptable acid addition salts for the compound of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like.

The compositions of the present invention include suspensions, solutions, elixirs, aerosols, or solid dosage forms. Carriers such as starches, sugars, microcrystalline cellulose, diluents, granulating agents, lubricants, binders, disintegrating agents, and the like are suitable in the case of oral solid preparations (such as powders, capsules, and tablets), and oral solid preparations are preferred over the oral liquid preparations. The most preferred oral solid preparation is a tablet.

Because of their ease of administration, tablets and capsules represent the most advantageous oral dosage unit form, in which case solid pharmaceutical carriers are employed. If desired, tablets may be coated by standard aqueous or nonaqueous techniques.

In addition to the common dosage forms set out above, the compounds of the present invention may also be administered by controlled release means and delivery devices such as those described in U.S. Pat. Nos.: 3,845,770; 3,916,899; 3,536,809; 3,598,123; and 4,008,719, the disclosures of which are hereby incorporated by reference.

Pharmaceutical compositions of the present invention suitable for oral administration may be presented as discrete units such as capsules, cachets, tablets, or aerosol sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active agent or dispersing agent. Molded tablets may be made by molding in a suitable machine, a mixture of the powdered compound moistened with an inert liquid diluent. Desirably, each tablet contains from about 2 mg to about 10 mg of the active ingredient, and each cachet or capsule contains from about 2 mg to about 10 mg of the active ingredient. Most preferably, the tablet, cachet or capsule contains either one of three dosages, about 2 mg, about 5 mg and about 10 mg of (+) cetirizine dihydrochloride for oral administration.

The invention is further defined by reference to the following examples describing in detail the preparation of the compound and the compositions of the present invention, as well as their utility. It will be apparent to those skilled in the art, that many modifications, both to materials, and methods, may be practiced without departing from the purpose and interest of this invention.

EXAMPLES

Example 1

The antihistaminic activity of the racemate and enantiomers of cetirizine is studied in receptor binding assays with washed guinea pig brain and lung tissue membranes following the procedure of Snyder and Snowman (op cit). The tissues are used to establish inhibitory concentration values expressed in micromolar concentration ($IC_{50}$) for racemic cetirizine and its enantiomers to inhibit the binding of tritiated mepyramine. The selection of these tissues provides information as to the binding at central and peripheral $H_1$ histamine receptors. The specificity of the $H_1$-receptor binding may then be compared with the binding at radio ligand labeled receptors for other central mediators.

Example 2

The antihistaminic activity of the isomers of Cetirizine is also studied in vitro in the guinea pig ileum preparation described by Staff [*Pharmacological Experiments on Isolated Preparations*, E & S. Livingstone Ltd., Edinburgh (1968).].

Example 3

Cetirizine isomer activity is also studied in isolated guinea pig tracheobronchial smooth muscle preparation according to the method of Campoli-Richards, et al. [*Drugs* 40, 762–781 (1990)] and Wardell, et al. [*J. Pharm. Exp. Ther.* 167–184 (1974)]. These preparations demonstrate competitive antagonism to histamine-induced contractions in a model relevant to the inhibition of histamine-induced disorders in vivo. The primary antihistaminic activity is then compared to the relative anticholinergic activities ("adverse effects") of cetirizine in the same tissue. The anticholinergic activity is evaluated by challenging the tissue with a cholinergic agent.

Example 4

Single ventricular myocytes are obtained from isolated cat hearts by conventional techniques. The rod-shaped single cells are maintained in a HEPES buffer and they are "patch clamped" using suction pipettes. A Patch-Clamp L/M-PEC 7 amplifier is used to record current tracings, and the recording electrodes are filled with a solution of potassium aspartate. Voltage clamp pulses and data acquisition are controlled by a Sperry PC/IT Computer running P Clamp software. A minimum of 4 cells are studied at each test concentration of the following drugs: racemic cetirizine, (+) cetirizine, (−) cetirizine and quinidine (as a reference compound).

ORAL FORMULATION
Capsules:

| Formula | Quantity per capsule in mg | | |
|---|---|---|---|
| | A | B | C |
| (+) Cetirizine | 2.0 | 5.0 | 10.0 |
| Lactose | 103.75 | 100.75 | 95.75 |
| Cornstarch | 18.75 | 18.75 | 18.75 |
| Magnesium Stearate | 0.50 | 0.50 | 0.50 |
| Compression Weight | 125.0 | 125.0 | 125.0 |

The (+) cetirizine, lactose and cornstarch are blended until uniform and then the magnesium stearate is blended into the resulting powder, which is sieved and filled into suitably sized, two-piece, hard gelatin capsules using conventional machinery. Other doses may be prepared by altering the fill weight and, if necessary, changing the capsule size to suit.

ORAL FORMULATION
Tablets:

| Formula | Quantity per tablet in mg | | |
|---|---|---|---|
| | A | B | C |
| (+) Cetirizine | 2.0 | 5.0 | 10.0 |
| Lactose | 70.75 | 67.75 | 62.75 |
| Cornstarch | 3.0 | 3.0 | 3.0 |
| Water (per thousand Tablets)* | 30.0 mL | 30.0 mL | 30.0 mL |
| Cornstarch | 18.75 | 18.75 | 18.75 |
| Magnesium Stearate | 0.50 | 0.50 | 0.50 |
| Compression Weight | 125.0 | 125.0 | 125.0 |

*The water evaporates during manufacture

The (+) cetirizine is blended with the lactose until a uniform blend is formed. The smaller quantity of cornstarch is blended with the water to form the resulting corn starch paste. This is then mixed with the uniform blend until a uniform wet mass is formed. The remaining cornstarch is added to the resulting wet mass and mixed until uniform granules are obtained. The granules are then screened through a suitable milling machine, using a ¼ inch stainless steel screen. The milled granules are dried in a suitable drying oven until the desired moisture content is obtained. The dried granules are then milled through a suitable milling machine, magnesium stearate is blended in, and the resulting mixture is compressed into tablets of the desired shape, thickness, hardness and disintegration. Tablets of other strengths may be prepared by altering the ratio of active ingredient to the excipients or to the final weight of the tablet.

What is claimed is:

1. A method of treating chronic and physical urticaria in a human which comprises administering to a human in need of such therapy an amount of (+) cetirizine, or a pharmaceutically acceptable salt thereof, substantially free of its (−) stereoisomer, said amount being sufficient to alleviate symptoms of chronic and physical urticaria.

2. A method of treating chronic and physical urticaria in a human, while avoiding the concomitant liability of sedation associated with racemic cetirizine, which comprises administering to a human in need of such therapy an amount of (+) cetirizine, or a pharmaceutically acceptable salt thereof, substantially free of its (−) stereoisomer, said amount being sufficient to alleviate symptoms of chronic and physical urticaria but insufficient to cause said sedation.

3. The method of claim 2 wherein (+) cetirizine is administered by transdermal delivery.

4. The method of claim 3 wherein the amount of (+) cetirizine or a pharmaceutically acceptable salt thereof administered is from about 1 mg to about 25 mg per day.

5. The method of claim 2 wherein the amount of said (+) cetirizine or a pharmaceutically acceptable salt thereof, substantially free of its (−) stereoisomer, is administered together with a pharmaceutically acceptable carrier.

6. The method according to claim 2, wherein (+) cetirizine is administered as a hydrochloride salt.

* * * * *